US008017143B2

(12) United States Patent  (10) Patent No.: US 8,017,143 B2
Shin et al.  (45) Date of Patent: Sep. 13, 2011

(54) COATING AGENT FOR DRUG RELEASING STENT, PREPARATION METHOD THEREOF AND DRUG RELEASING STENT COATED THEREWITH

(75) Inventors: Kyong-Min Shin, Seoul (KR); Dong-ki Lee, Seongnam-si (KR); Don-haeng Lee, Seoul (KR); Kun Na, Bucheon-si (KR); Eun-ae Jo, Seoul (KR)

(73) Assignees: Taewoong Medical Co., Ltd, Kyunggi-do (KR); Kyoung-Min Shin, Seoul (KR)

( * ) Notice: Subject to any disclaimer, the term of this patent is extended or adjusted under 35 U.S.C. 154(b) by 578 days.

(21) Appl. No.: 12/154,864

(22) Filed: May 28, 2008

(65)  Prior Publication Data
US 2008/0300296 A1  Dec. 4, 2008

(30)  Foreign Application Priority Data

Jun. 1, 2007  (KR) .................. 10-2007-0053877
Oct. 12, 2007  (KR) .................. 10-2007-0103080

(51) Int. Cl.
*A61K 31/337* (2006.01)
*A61K 47/36* (2006.01)
*A61K 47/34* (2006.01)

(52) U.S. Cl. ...... 424/426; 514/449; 514/777; 514/772.3
(58) Field of Classification Search .................. None
See application file for complete search history.

(56)  References Cited

U.S. PATENT DOCUMENTS

2005/0220835 A1* 10/2005 Jayaraman et al. ........... 424/423
* cited by examiner

*Primary Examiner* — Robert A Wax
*Assistant Examiner* — Danah Al-Awadi
(74) *Attorney, Agent, or Firm* — IP & T Group LLP (57)  ABSTRACT

Disclosed are a coating agent for drug releasing stents, a method for preparing the same and a drug releasing stent coated therewith. The coating agent comprises a biologically active material and a coating material selected from among pullulan acetate, represented by the following Chemical Formula 1, and a polyurethane-surfactant mixture.

[Chemical Formula 1]

-continued

2 Claims, 3 Drawing Sheets

COATING AGENT FOR DRUG RELEASING STENT, PREPARATION METHOD THEREOF AND DRUG RELEASING STENT COATED THEREWITH

BACKGROUND OF THE INVENTION

1. Field of the Invention

The present invention relates to a coating agent for drug releasing stents, a method for preparing the same and a drug releasing stent coated therewith. More particularly, the present invention relates to a coating agent for use in stents capable of controlled drug release, a preparation method thereof, and a drug releasing stent coated therewith.

2. Description of the Related Art

A stent is a tubular prosthesis or support, which is now widely used to hold open a natural conduit, such as a lumen, vessel, etc., to allow access for surgery or related invasive chemical treatment and to prevent the stenosis of the conduit. Furthermore, the insertion and expansion of a stent within the esophagus, the respiratory organs, the vessels, the urinary organs, and other lumens which are difficult to access has proven an influential therapy for diseases occurring therein.

A colo-rectal stent, developed in the late 1990's, can be used instead of an artificial anus for a patient who has undergone a surgical operation for rectal cancer. However, colorectal stents are not applicable to all patients who have undergone surgical operations for rectal cancer. Stent implantation is not a therapy for cancer, but a temporary treatment for preventing or counteracting disease-induced localized flow constriction, e.g., the narrowing of the intestine due to cancer. Typically, a colo-rectal stent is a tube made from metal wires, which is designed for insertion into a narrowed region of the large intestine and expansion thereat to counteract the flow constriction. For example, stents applicable to patients with colorectal cancer are commercially available in various types, and are most often made of a nickel and titanium alloy (commonly referred to as "Nitinol").

Recently, many attempts have been made to improve therapeutic effects with stents, i.e., stent implants capable of delivering drugs, such as thrombolytic agents or antihyperplasia agents. For example, U.S. Pat. No. 5,092,877 discloses self-expanding stents to which drug release coatings are applicable. Also, PCT Publication No. WO 1996/032907 describes a drug release coated stent.

In order to release a biologically active material over a long period, a method for coating a stent with a drug has been studied. Typically, the biologically active material is dissolved in a polymeric solvent and the solution is applied to a stent, followed by removing the solvent to afford a biologically active material-coated stent.

When a biologically active material, such as dexamethasone, is selected for use in application to stents, attention must be paid to miscibility and compatibility with the solvent or polymers used and to the release rate.

Korean Patent No. 10-439156 discloses a coating composition for drug release stents and a preparation method thereof, in which a coating composition comprising 0.01-30 wt % of a co-precipitation of a biologically active material selected from dexamethasone, paclitaxel and mitomycin with a water-soluble polymer and 70-99.99 wt % of a crosslinking polymer solvent is applied to a stent.

Korean Patent. No. 10-511618 discloses a multi-layer coating for drug release-controllable stents and a method for the preparation thereof. The multi-layer structure is composed of a base layer made of poly(ethylene-co-vinylacetate) or styrenic rubber polymer, a second coating layer made of a biocompatible polymer and a drug, and a third coating layer made of a different drug. Examples of the biocompatible polymer include polyvinylalcohol, polyethylene glycol, polylactide, polyglycolide, polylactide copolymer, polyethylene oxide, polydioxanone, polycaprolactone, polyphosphagen, polyanhydride, polyaminoacid, cellulose acetate butylate, cellulose triacetate, polyacrylate, polyacrylamide, polyurethane, polysiloxane, polyvinylpyrrolidone, and copolymers thereof. The drug used in the second layer may be selected from among anti-platelet agent containing cilostazol (6-[4-(1-cyclohexyl-1Htetrazol-5-yl)butoxy]-3,4-dihydro-2 (1H)-quinolinone, empirical formula $C_{20}H_{27}N_5O_2$, Mw 369.47), an anti-thrombolytic agent, an antihyperplasia agent, a growth factor, an antioxidant and a radio-active agent.

SUMMARY OF THE INVENTION

It is an object of the present invention to provide a release-controllable coating agent for drug-releasing stents, a method for the preparation thereof, and a drug releasing stent coated therewith.

In accordance with an aspect thereof, the present invention provides a coating agent for drug releasing stents, comprising a biologically active material and a coating material selected from among a pullulan acetate, represented by the following Chemical Formula 1, and a polyurethane-surfactant mixture.

[Chemical Formula 1]

Preferably, the biologically active material may be taxol.

When the coating material is pullulan acetate, the biologically active agent may be used in an amount of 0.01-1 weight parts per weight part of pullulan acetate.

In the coating agent, in which the coating material is a polyurethane-surfactant mixture, the surfactant is present in an amount of 5-30 weight % based on the weight of the polyurethane.

When the coating material is a polyurethane-surfactant mixture, the biologically active material is used in an amount of 5 weight % based on the weight of the polyurethane.

In accordance with another embodiment of the present invention, there is provided a method for preparing a coating agent for drug releasing stents, comprising: (1) dissolving 300 mg of pullulan acetate, having 3-27 acetyl group for every 10 anhydroglucose units of pullulan, in 2-4 ml of methylene chloride to afford a pullulan acetate solution; and (2) dissolving a biologically active material in the pullulan acetate solution in an amount from 0.01 to 1 weight parts per weight part of pullulan acetate.

In accordance with a further embodiment of the present invention, there is provided a method for preparing a coating agent for drug releasing stents, comprising: (1) dissolving 400 mg of polyurethane in 21 ml of tetrahydrofuran to afford a first solution; (2) dissolving a surfactant in an amount of 5-30 weight % and a biologically active material in an amount of 5 weight %, based on the weight of polyurethane, in 21 ml of tetrahydrofuran to afford a second solution; and (3) mixing the first solution with the second solution.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Below, a detailed description will be given of the present invention, with reference to the drawings.

In accordance with an aspect thereof, the present invention pertains to a coating agent for drug releasing stents. The coating agent according to the present invention is in the form of nanoparticles comprising a coating material selected from among pullulan acetate, represented by the following Chemical Formula 1, and a polyurethane-surfactant mixture, with a biologically active agent entrapped therein.

[Chemical Formula 1]

Pullulan acetate may be prepared by acetylating pullulan. Pullulan is represented by the following Chemical Formula 2.

[Chemical Formula 2]

Pullulan is an extracellular polysaccharide polymer, produced from starch by the fungus *Aureobasidium pullulans*, consisting of maltotriose units, in which three glucose units in maltotriose are connected by an α-1,4 glycosidic bond, whereas consecutive maltotriose units are connected to each other by an α-1,6 glycosidic bond. This polysaccharide polymer is extensively studied for use as biomaterials through chemical modification. The Sunamoto Group in Japan constructed self-aggregates of cholesterol-bearing pullulan and studied their physicochemical properties. In the present invention, amphiphilicity is introduced into such pullulan by acetylation as follows. First, 2 g of pullulan was dissolved in 20 ml of formamide at 50° C. with strong stirring. To the solution were added 6 ml of pyridine and 315 ml of acetic anhydride, followed by reaction at 54° C. for 48 hrs. The product was recovered through precipitation in 200 ml of water and subsequent filtration. This process was conducted three or more times to remove impurities from the product.

Polyurethane is a compound represented by the following Chemical Formula 3.

[Chemical Formula 3]

Polyurethane, as shown in Chemical Formula 3, is a polymer consisting of a chain of organic units joined by urethane links between an alcohol (—OH) group of a diol and an isocyan group (NCO) of isocyanate.

The surfactant used in the present invention is preferably Pluronic F-127, represented by the following Chemical Formula 4.

[Chemical Formula 4]

wherein n is an integer of 100 and y is an integer of 65.

In a pluronic solution, the biologically active material can be more evenly dispersed.

The biologically active material may be taxol. Taxol was discovered from the bark of the Pacific yew tree, *Taxus brevifolia*, in a National Cancer Institute program for developing anticancer agents from various natural materials of animals, plants and minerals. Intensive attention began to be paid to taxol due to the anticancer activity thereof in early 1979, and it was approved by the FDA in 1993. At first, because of the difficulty in chemically synthesizing taxol due to the characteristic structure thereof, obtaining taxol entailed fouling the environment. Currently, the partial synthesis of taxol is possible, so that its material can be easily secured. Taxol has no influence on the synthesis of DNA and RNA in cancer, nor does it damage DNA molecules, but it selectively acts on tubulin. Taxol interferes with the normal function of microtubule breakdown by binding to tubulin. The binding of taxol locks these building blocks in place. The resulting microtubule/taxol complex does not have the ability to disassemble, arresting the cell division cycle at the metaphase, which leads to the death of cancer cells. Clinical tests conducted thus far report that taxol has excellent therapeutic effects on esophageal cancer, prostate cancer, rectal cancer, bladder cancer, hepatic tumors, central nervous system tumors, brain tumors, etc. The side effects of taxol, caused by myelosuppression, leading to a decrease in leukocyte level, occur 8-10 days after the administration thereof, and disappear between 15 and 21 days after the administration. Serious depilation, peripheral neuropathy, and muscle pain are also reported as side effects.

When pullulan acetate is employed as a coating material, the biologically active material is used in an amount from 0.01 to 1 weight parts based on one weight part of pullulan acetate. If the biologically active material is used in an amount less than 0.01 weight part per weight part of pullulan acetate, its activity, for example, the anticancer activity of taxol, is insufficient. On the other hand, if the amount of the biologically active material exceeds 1 weight part, it is not completely applied to a stent by the coating material.

When a mixture of polyurethane-surfactant is employed as a coating material, the surfactant is used in an amount from 5 to 30 weight % on the basis of the total weight of polyurethane. If the surfactant is used in an amount less than 5 weight %, the biologically active material, i.e. taxol, is released at too low a rate to exert the biologically useful activity, e.g., anticancer activity. On the other hand, if the amount of the surfactant is over 30 weight %, the early release rate of the biologically active material is too high to obtain a preferable result.

When a mixture of polyurethane-surfactant is employed as a coating material, the biologically active material is used in an amount of 5 weight % based on the total weight of the mixture of polyurethane-surfactant.

In accordance with another aspect thereof, the present invention pertains to a method for preparing a coating agent for drug-releasing stents, comprising (1) dissolving 300 mg of pullulan acetate having 3-27 acetyl groups per 10 anhydroglucose units of pullulan in 2-4 ml of methylene chloride to afford a pullulan acetate solution; and (2) dissolving a biologically active material in the pullulan acetate solution in an amount from 0.01 to 1 weight part per weight part of pullulan acetate.

In 2-4 ml of methylene chloride is dissolved 300 mg of pullulan acetate having 3-27 acetyl groups per 10 anhydroglucose units of pullulan. When the acetylation degree of pullulan is below 3, the coating agent is soluble in water. On the other hand, when the acetylation degree is over 27, the coating agent is significantly decreased in flexibility.

The coating agent is obtained by adding a biologically active material to the pullulan acetate solution in an amount of 0.01-1 weight parts per weight part of pullulan acetate and stirring the solution. When the concentration of the biologically active material is below 0.01%, the activity of the biologically active material, such as anticancer activity, is not sufficiently exhibited. On the other hand, when the concentration of the biologically active material is over 1%, it is not completely entrapped within the polymer.

In accordance with a further aspect thereof, the present invention pertains to a method for preparing a coating agent for drug releasing stents, comprising: (1) dissolving 400 mg of polyurethane in 21 ml of tetrahydrofuran to afford a first solution; (2) dissolving a surfactant in an amount of 5-30 weight % and a biologically active material in an amount of 5 weight %, based on the weight of polyurethane, in 21 ml of tetrahydrofuran to afford a second solution; and (3) mixing the first solution with the second solution.

In 21 ml of THF is dissolved 400 mg of polyurethane to give a standard polyurethane solution.

Preferably, Pluronic F-127 and taxol are used as the surfactant and the biologically active material, respectively. Based on the weight of polyurethane, Pluronic F-127 and taxol are used in amounts of 5-30 weight % and 5 weight %, respectively.

The coating agent for drug releasing stents is obtained by mixing the first solution with the second solution.

A better understanding of the present invention may be grasped with reference to the following examples, which are set forth to illustrate, but are not to be construed to limit the present invention.

Synthesis Example 1

The following reagents were used.

Pullulan (Mw 100,000 Da) was purchased from Hayashibara, Japan. Acetic anhydride pyridine was purchased from Sigma. The other reagents used in the present invention were of a commercially available special grade which was used without additional purification. Taxol was purchased from Samyang Genex, Korea.

Pullulan acetylation was conducted as follows.

Amphiphilicity was imparted to pullulan by acetylation. In this regard, 2 g of pullulan was dissolved at 50° C. in 20 ml of formamide with strong stirring. To this solution were added 6 ml of pyridine and 315 ml of acetic anhydride, followed by reaction at 54° C. for 48 hrs. After completion of the reaction, 200 ml of water was added to afford the product as a precipitate which was then filtered. This procedure was repeated three times to remove impurities from the product. The acetylation degree of the pullulan acetate thus synthesized was measured using FR-IR, NMR, and GPC (gel permeation chromatography).

In 3 ml of methylene chloride was dissolved 300 mg of pullulan acetate having 15 acetyl groups for every 10 anhydroglucose units of pullulan to afford a pullulan acetate solution. A biologically active material was added in an amount of 10-20 weight % to the pullulan solution, after which vortexing was conducted until the biologically active material was completely dissolved.

Example 1

Using a dipping method, a stent was coated with the coating agent obtained in Synthesis Example 1. Because the drug was evenly dissolved in pullulan acetate, it could be uniformly applied to the stent simply by dipping. A Teflon-coated stent was used. First, Teflon was coated 30 μm thick. Five rounds of coating were conducted, and the thickness was measured every coat. The thickness was measured to be 35 μm after the first round of coating, 41 μm after the second round of coating, 47 μm after the third round of coating, 53 μm after the fourth round of coating, and 63 μm after the fifth round of coating.

Preparation Example 1

400 mg of polyurethane (PU) was sufficiently dissolved in 21 ml of tetrahydrofuran and the resulting solution was used as a standard PU solution. This standard PU solution, free of pluronic, was used to compare the drug release rates with those of PU solutions containing pluronic. A coating agent was obtained by dissolving 20 mg of taxol (5% of polyurethane) in the standard PU solution or in a polyurethane solution containing pluronic.

Preparation Example 2

A pluronic 5% coating agent was prepared, in which pluronic was added in an amount of 5% based on the total weight of the standard PU solution of Preparation Example 1, that is, in an amount of 20 mg. The polyurethane concentration was decreased by an extent corresponding to the amount of the pluronic that was added. That is, a coating agent comprising 380 mg of polyurethane and 20 mg of pluronic was prepared. Separately, a biologically active material was dissolved, along with pluronic, in tetrahydrofuran, and mixed with the polyurethane solution to afford a 5% coating agent.

Preparation Example 3

A 10% coating agent was prepared in the same manner as in Preparation Example 2, with the exception that the pluronic was used in an amount of 40 mg.

Preparation Example 4

A pluronic 20% coating agent was prepared in the same manner as in Preparation Example 2, with the exception that the pluronic was used in an amount of 80 mg.

Preparation Example 5

A pluronic 30% coating agent was prepared in the same manner as in Preparation Example 2, with the exception that the pluronic was used in an amount of 120 mg.

Example 2

Each of the coating agents for drug releasing stents prepared in the Preparation Examples was poured into a circular Teflon frame, followed by evaporating the solvent to afford a film. The solvent, tetrahydrofuran, is volatile. Evaporation was conducted naturally because artificial operation for fast evaporation carries the danger of the formation of bubbles in the film.

Experimental Example 1

Figure 1:
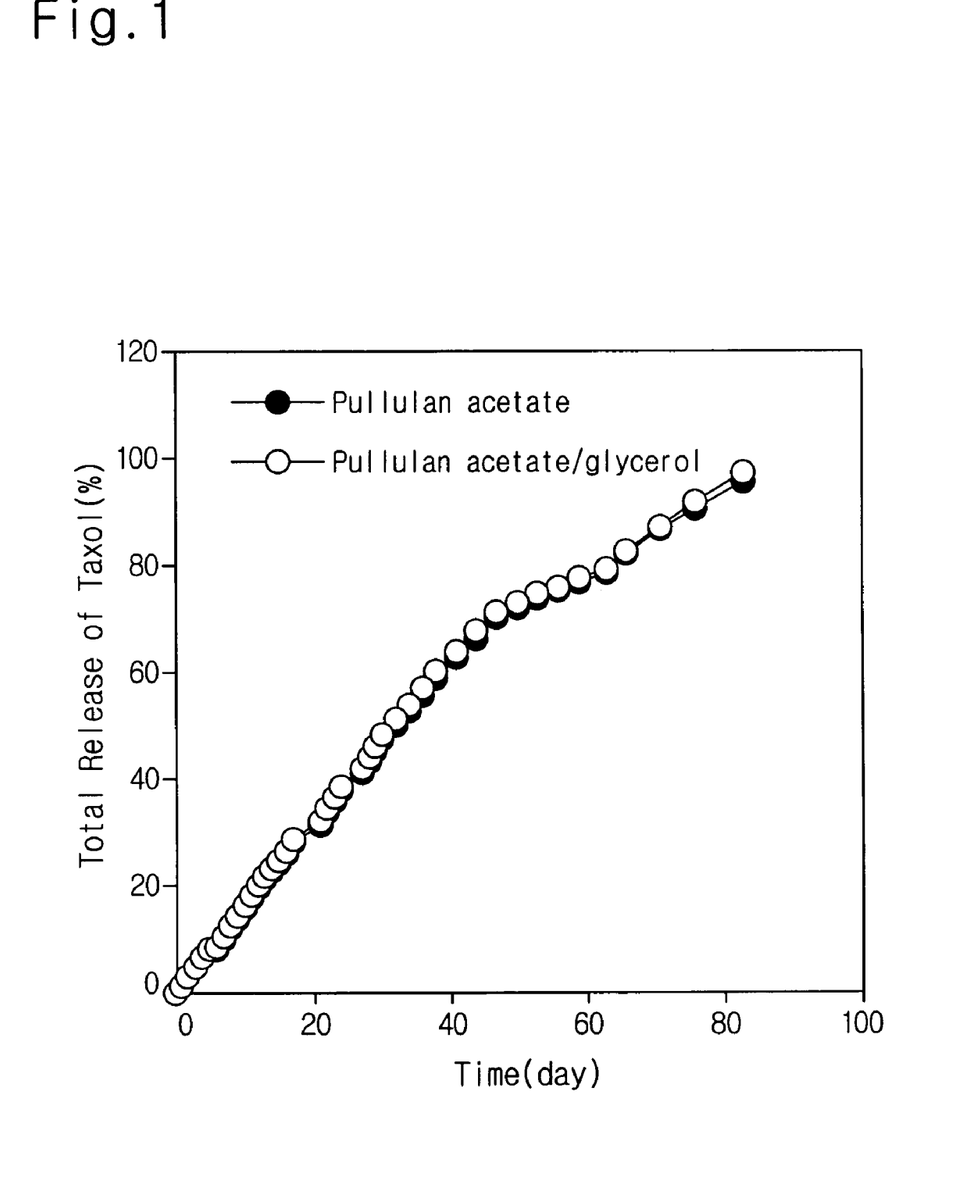
FIG. 1 is a graph showing the releasing properties of taxol from the pullulan acetate films, in which pullulan acetate is used as a coating material in accordance with the present invention.

The pullulan acetate films formed in Example 1 were tested for the release properties of taxol through HPLC, and the results are shown in FIG. 1.

Under the following analysis conditions, the test was conducted.

The HPLC system used in this test included a Finnigan gradient pump as an injection pump, Hypersil Gold PFP (C18, 5 μm, 150×4.6 mm) as a column, and Waters 486 Tunable Absorbance detector (228 nm) as an detector. A mixture of 65/35 acrylonitrile/water was used as a solvent at a flow rate of 1.5 ml/min. The operation time was set to be 3.5 min. The initial injection volume was 50 μl. A Waters 717 plus autosampler was used with multichrom software included therein.

As seen in FIG. 1, the release of taxol from the pullulan acetate films was linearly increased in a time-dependent manner.

Experimental Example 2

The pullulan acetate films formed in Example 1 were applied to 6-week-old Balb/C male mice weighing 20-30 g to measure the change of tumor volumes with time. The results are shown in FIG. 2.

Figure 2:
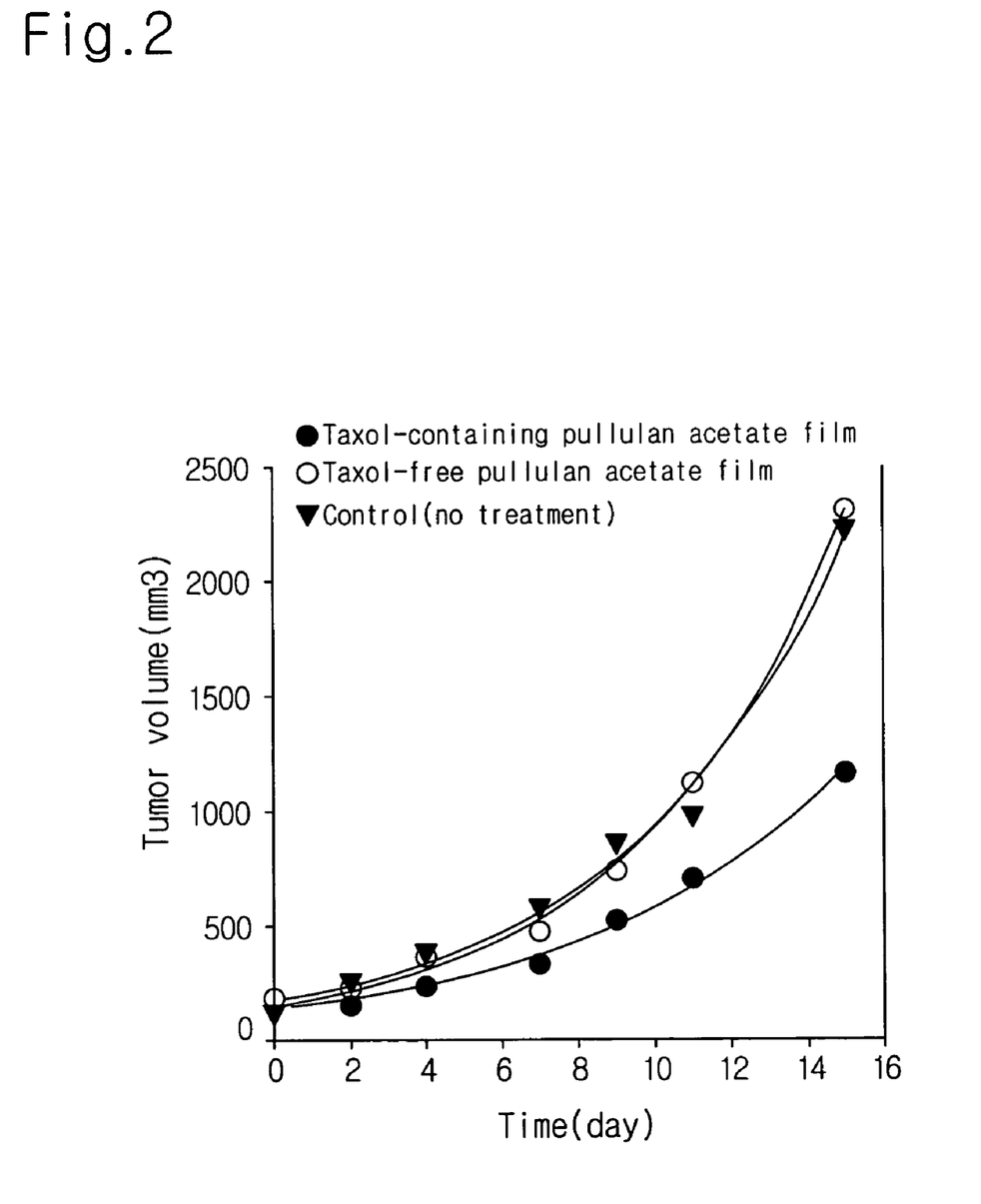
FIG. 2 is a graph showing cancer sizes plotted against time upon in vivo application of the coating agents, in which pullulan acetate is used as a coating agent in accordance with the present invention.

In FIG. 2, comparison 1 denotes a group treated with a pullulan acetate film containing no taxol, while the control is a non-treatment group.

As seen in FIG. 2, the tumor size of the mice treated with the p pullulan acetate film containing taxol was significantly decreased compared with that of the comparison 1 and the control, indicating that the anticancer agent taxol is effectively released into the body from the film.

Experimental Example 3

Each of the films formed in Example 2 was cut to ¼ of its original size, and the smaller film pieces were placed into respective tubes containing 3 ml of 0.01M PBS to allow the drug to be released from the tube. The pH of the buffered solution was adjusted to 7.4, similar to the pH in the body. The release test was conducted at 37° C. for a total of 40 days, with the buffer exchanged with fresh buffer every day for the first 20 days and then every two days thereafter. The release test results of five kinds of coating agents for drug releasing stents are shown in FIG. 3.

Figure 3:
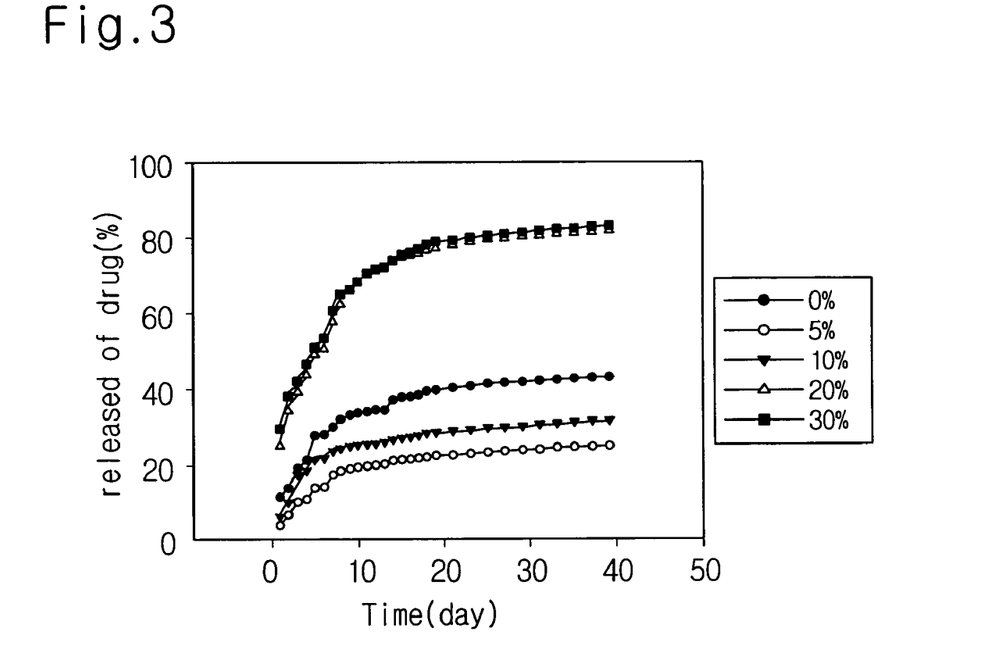
FIG. 3 is a graph showing drug release patterns of coating agents, comprising polyurethane-surfactant as a coating material, for drug releasing stents, and a control comprising polyurethane alone as a coating material.

As shown in FIG. 3, the coating agent containing the surfactant at a concentration of 20% or 30% was found to have a higher drug release rate than that of the coating agent devoid of the surfactant, while the coating agent containing the surfactant at a concentration of 10% or 20% had a lower drug release rate. Thus, the drug release rate can be modulated by adjusting the amount of the surfactant.

Experimental Example 4

Figure 4:
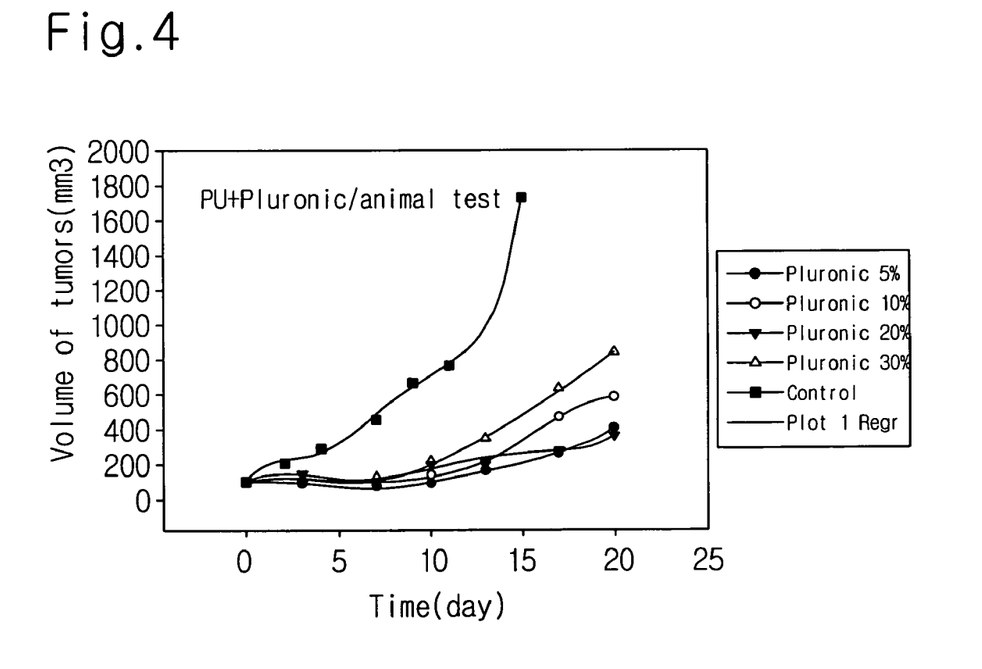
FIG. 4 is a graph in which cancer sizes are plotted against time upon treatment with coating agents, comprising polyurethane-surfactant as a coating material, for drug releasing stents according to the present invention and a control comprising polyurethane alone.

Various dosage forms of coating agents, whether containing pluronic and/or taxol, were assayed for anticancer activity in small animals (rats) by monitoring cancer sizes after the administration thereof, and the results are depicted in FIG. 4. Four experimental rats were assigned to each experiment group.

As seen in FIG. 4, the small animals underwent changes in tumor size depending on the concentration of pluronic and there was a distinctive difference in anticancer effect between coating agents containing and not containing pluronic. As seen in FIG. 4, a greater reduction in cancer size was observed upon treatment with coating agents containing 5% or 20% pluronic than other amounts of pluronic. However, all of the coating agents containing pluronic significantly decreased cancer size compared to the control containing no pluronic. The anticancer effect of pluronic is believed to be attributed to the ability thereof to transform with temperature. Pluronic features a phase change, by which it is in a hydrophobic form at high temperatures and in a liquid state at low temperatures. Hence, pluronic, when introduced into the body, undergoes phase transition into a hydrophobic state due to the increased temperature, emitting the biologically active material dissolved together therewith, and thus exhibiting a release effect. However, a higher pluronic concentration allows the drug to be released faster, thus reducing the therapeutic effect. Despite this concept, the best anticancer effect was observed at a pluronic concentration of 20%, indicating that this pluronic concentration is optimal for stent coating.

As described hereinbefore, a drug release-controllable coating agent is provided for drug releasing stents in accordance with the present invention. Also, a method for preparing the coating agent and a drug releasing stent coated with the coating agent are provided.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing a coating agent for drug releasing stents, comprising:
    (1) dissolving 300 mg of pullulan acetate, having 3-27 acetyl groups for every 10 anhydroglucose units of pullulan, in 2-4 ml of methylene chloride to afford a pullulan acetate solution; and
    (2) dissolving a biologically active material in the pullulan acetate solution in an amount from 0.01 to 1 weight parts per weight part of pullulan acetate.

2. A method for preparing a coating agent for drug releasing stents, comprising:
    (1) dissolving 400 mg of polyurethane in 21 ml of tetrahydrofuran to afford a first solution;
    (2) dissolving a surfactant in an amount of 5-30 weight % and a biologically active material in an amount of 5 weight %, based on the weight of polyurethane, in 21 ml of tetrahydrofuran to afford a second solution; and
    (3) mixing the first solution with the second solution;
    wherein the surfactant is a compound represented by:

wherein n is an integer of 100 and y is an integer of 65.

* * * * *

UNITED STATES PATENT AND TRADEMARK OFFICE
CERTIFICATE OF CORRECTION

PATENT NO. : 8,017,143 B2
APPLICATION NO. : 12/154864
DATED : September 13, 2011
INVENTOR(S) : Kyong-Min Shin It is certified that error appears in the above-identified patent and that said Letters Patent is hereby corrected as shown below:

Title Page, Item (73) should read

ASSIGNEES: Taewoong Medical Co., Ltd, Kyunggi-do, (KR); Kyong-Min Shin, Seoul (KR)

Signed and Sealed this
Fifteenth Day of November, 2011

David J. Kappos
*Director of the United States Patent and Trademark Office*